United States Patent [19]

Makovec et al.

[11] 4,214,115

[45] Jul. 22, 1980

[54] ALKYLATION PROCESS UTILIZING PLURAL OLEFINIC REACTANTS

[75] Inventors: Donald J. Makovec; Thomas Hutson, Jr., both of Bartlesville, Okla.

[73] Assignee: Phillips Petroleum Company, Bartlesville, Okla.

[21] Appl. No.: 904,149

[22] Filed: May 9, 1978

[51] Int. Cl.² ............................................. C07C 3/54
[52] U.S. Cl. .................................. 585/716; 585/723
[58] Field of Search ................ 260/683.48, 683.43, 260/683.45; 585/716

[56] References Cited

U.S. PATENT DOCUMENTS 3,780,131  12/1973  Sobel ........................... 260/683.45

Primary Examiner—George Crasanakis

[57] ABSTRACT

A cyclic system for the alkylation of an isoparaffin, e.g., isobutane, wherein a first olefinic reactant, e.g., butylene, is used to alkylate the isoparaffin for a first period of time in an alkylation reactor and then a second olefinic reactant, e.g., propylene, is used to alkylate the isoparaffin for a second period of time in the same alkylation reactor. During the period that the isoparaffin is alkylated with the first olefinic reactant, the reactor effluent stream is continuously separated into a liquid hydrocarbon phase comprising alkylation products and unreacted isoparaffin and a liquid acid alkylation catalyst phase. The acid catalyst is continuously recycled to the reactor and the hydrocarbon phase is passed to a first surge zone or holding tank. During the second period of time, the isoparaffin-rich hydrocarbon phase from the first surge zone and the second olefinic reactant, along with continuously recycled catalyst, are charged to the same alkylation reactor so that, preferably, feed to the reactor is continuously effected. The reactor effluent is continuously separated into a liquid hydrocarbon phase containing unreacted isoparaffin and a liquid catalyst phase. The hydrocarbon phase is charged in part to fractionation and in part to a second surge zone. During the first period of time, hydrocarbon from the second surge zone is charged to this fractionation so the fractionation is continuously in operation. Isoparaffin is continuously removed from the fractionation to a third surge zone. Isoparaffin can be charged from the third surge zone to the alkylation reactor.

6 Claims, 1 Drawing Figure

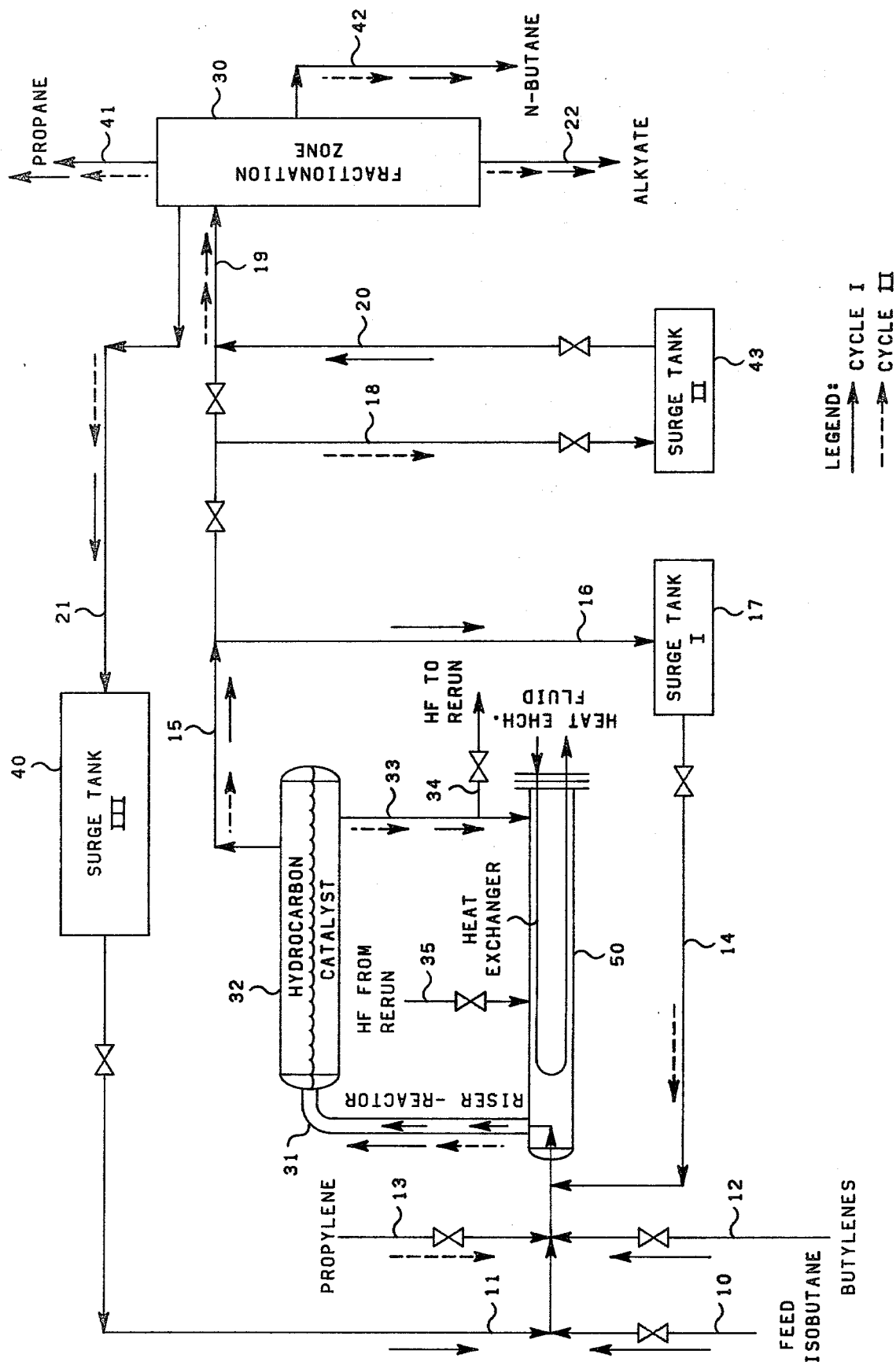

ALKYLATION PROCESS UTILIZING PLURAL OLEFINIC REACTANTS

BACKGROUND OF THE INVENTION

This invention relates to a process for alkylating an alkylatable isoparaffinic hydrocarbon with olefinic hydrocarbons. In another aspect, this invention relates to a process and apparatus for the alkylation of isoparaffins with two or more different olefins with a liquid acid alkylation catalyst. In yet another aspect, this invention further relates to a cyclic process for the alkylation of an isoparaffin with different olefins at different temperatures at different periods of time in the same reactor. In yet another aspect, this invention relates to the alkylation of an isoparaffin with a first olefinic reactant, continuously separating the resultant alkylation effluent into a first liquid hydrocarbon phase and a liquid acid phase, and continuously recycling the acid phase to the alkylation reactor, and, during the second period of time, recycling said first liquid hydrocarbon phase to be reacted with a second olefinic reactant. In still another aspect, this invention relates to a cyclic alkylation reaction wherein an isoparaffin is utilized cyclically with two different olefinic reactants in the same reactor at two different periods of time, and the acid catalyst is continuously separated during both periods of time, and being either heated or cooled to the optimum temperature required for each separate alkylation. In yet another aspect, this invention relates to an apparatus for the alkylation of an isoparaffin comprising only one alkylation reactor, three surge zones, and a fractionator for separating the various components of the alkylate stream.

Alkylation of isoparaffinic hydrocarbons, such as isobutane, isopentane, and the like, with olefinic hydrocarbons, such as propylene, butylene, amylenes, and the like, is well known as a commercially important method for producing gasoline boiling range hydrocarbons. Generally, the alkylation of isoparaffins with olefins is accomplished by contacting the reactants with an acid-acting catalyst, such as liquid hydrofluoric acid, settling the mixture to separate the liquid catalyst from the liquid hydrocarbons, and further separating the hydrocarbons, e.g., by fractionation, to recover alkylate product, and to recover unreacted isoparaffin for recycle to alkylation. The alkylate is typically a mixture of isomers of heptane, octane, etc., with the exact composition depending upon the isoparaffin and olefin reactants used. Various types of catalysts have been utilized in this reaction, including sulfuric acid, hydrofluoric acid, phosphoric acid, certain halosulfonic acids, and aluminum chloride. The preferred catalyst is hydrofluoric acid because of the relative ease with which it can be used and reused and because of the superior quality of the alkylate that is produced.

It is the usual practice to alkylate an isoparaffin with two different olefins in the same reactor at the same time, or in separate reactors, as it is known that separate alkylations of, for example, butylenes and propylene, produce higher octane total alkylate than the alkylate made by charging butylenes and propylene as combined olefins to the alkylation reactor. The processes disclosed in U.S. Pat. Nos. 3,158,661 and 3,787,518 exemplify an alkylation reaction wherein butylene olefin reactants and propylene olefin reactants are reacted in separate HF alkylation reactors. Due to the expense of providing separate reactors and settlers for the two different olefins, however, the economics of this type of process are not as favorable as a process in which only one alkylation reactor is necessary in order to obtain a high octane alkylate product. The advantage of the two-reactor alkylation system, however, is that one can control the individual reaction temperature as desired to allow each alkylation to run at the optimum temperature and thereby produce an optimum product.

U.S. Pat. No. 3,998,893 discloses a one-reactor system for the alkylation of olefins. The process involved, however, does not separate out the hydrofluoric acid catalyst from the hydrocarbon between olefin injections, and, therefore, must take the temperature from the first alkylation as a temperature to start the second alkylation. The process can only be used as effectively as a two-reactor system, therefore, if the optimum temperature for the first olefin to be alkylated is lower than that of the second olefin, otherwise, the process can have a detrimental effect on the quality of the alkylate product.

Accordingly, it is an object of the invention to provide an improved process and apparatus for alkylating one or more isoparaffins with at least two different olefins.

Another object of the present invention, is to provide an economical process in conjunction with a simplified apparatus for the alkylation of an isoparaffin with at least two different olefins.

Yet another object of the present invention is to provide an improved process for the alkylation of an isoparaffin with at least two different olefins wherein each olefin is reacted at the optimum temperature.

Another object of the present invention is to provide an economical process and simplified apparatus for the alkylation of an isoparaffin with at least two different olefins wherein the olefins can be reacted separately and at their optimum temperature in the same reactor.

Other objects, aspects, and the several advantages of this invention will be apparent to those skilled in the art upon a study of this disclosure, the appended claims, and the drawing.

SUMMARY OF THE INVENTION

This invention relates to a cyclic alkylation system wherein a first olefin reactant is used to alkylate an isoparaffin for a period of time, or "part-cycle," in an alkylation reactor and then a second olefin reactant is used to alkylate the isoparaffin in the same alkylation reactor for a period of time, or "part-cycle." Any cycle can be used, within reason, and the times of each "part-cycle" do not have to be equal. The length of each "part-cycle" will depend on the quantities of olefin reactants available. The acid alkylation catalyst is separated during each particular alkylation thereby allowing the catalyst to be cooled or heated so that upon recycle the catalyst will be at the optimum temperature for the particular olefin reactant used in the alkylation.

The present invention allows one to separately alkylate an isoparaffin most efficiently with two different olefin reactants in order to obtain a high octane alkylate product with the economy of a single reactor system. Although the alkylation is run in a single reactor, the desirable result obtained with a two-reactor system is still possible in that each alkylation is run at its optimum temperature no matter which olefin is reacted first.

The preferred olefin reactants used are the butylenes and propylene, and the preferred isoparaffin is isobutane. The continuous, periodic process begins by reacting the butylenes with the feed and recycle isobutane in admixture with an acid alkylation catalyst in an alkylation reactor. The reactor effluent is continuously separated into a hydrocarbon phase and an acid catalyst phase which is recycled to the reactor, and with the hydrocarbon phase being passed on to a first surge zone. The second part of the cycle or periodic process then commences with the reaction of propylene with the hydrocarbon phase stored in the first surge zone, this hydrocarbon being rich in unreacted isoparaffin. The hydrocarbon from the first surge zone is used as the isoparaffin source for the second part of the cycle. If additional isobutane is needed it can be obtained from another source and added to the alkylation reaction. Preferably, all of the reactant or feed isoparaffin is added during the first cycle. The reactor effluent is then continuously separated into a hydrocarbon phase and a catalyst phase. The catalyst is continuously recycled to the reactor after appropriate heating or cooling. The hydrocarbon phase from this second alkylation is, in part, charged to a second surge zone and, in part, to the fractionation zone. During the first period or cycle, hydrocarbon from the second surge zone is passed to this fractionation, thusly the fractionation is continuously in operation. During the first period, recycle isoparaffin is charged to the reactor from a third surge zone, said third surge zone continuously receiving the isoparaffin from the continuously operated fractionation zone. Alkylate product, light hydrocarbons, e.g., propane, and, preferably, vaporous normal butane, are each continuously recovered from the fractionation. After the second cycle is finished, the first cycle is repeated.

The cycle can also be reversed as the propylene alkylate containing the isobutane can be stored in surge zone 1 during the first "part-cycle," and then, in the second "part-cycle," the butylenes can be used as the olefinic reactant.

BRIEF DESCRIPTION OF THE DRAWING

The FIGURE shows a schematic of the cyclic material flow within a specific embodiment of the present invention.

DETAILED DESCRIPTION OF THE INVENTION

This invention relates to the alkylation process and apparatus whereby two different olefinic reactants, e.g., a lighter olefinic reactant and a heavier olefinic reactant, can be alkylated separately with an isoparaffin at the preferred alkylation conditions for each of the two olefins in a single alkylation reactor. The process is a cyclic process wherein a first olefinic reactant is reacted with the isoparaffin using excess isoparaffin and then the second olefinic reactant is reacted with the isoparaffin in the same, single alkylation reactor.

The first olefinic reactant, for example, butylenes, is alkylated during a first time period of alkylation with an isoparaffin, for example, isobutane, which isoparaffin includes reactant isoparaffin for both cycles plus excess isoparaffin for the desired isoparaffin/olefin ratio, in admixture with an acidic alkylation catalyst, e.g., hydrofluoric acid, in an alkylation zone. The resulting reactor effluent is continuously separated into a liquid hydrocarbon phase and a liquid acid phase with the hydrocarbon phase being passed to a first surge zone. The liquid acid phase is continuously recycled to the reactor. The surge zone is a storage tank for storing the hydrocarbon phase from the butylenes alkylation, which hydrocarbon comprises alkylate product and unreacted excess isoparaffin, until it is needed in the second time period of alkylation. The alkylate continues to accumulate in the surge zone throughout the alkylation reaction of the first olefinic reactant. The HF acid catalyst is continuously recycled to the reactor, being either heated or cooled in order to place it at the optimum temperature for the olefinic reactant used in the particular alkylation reaction to which the HF acid catalyst is to be recycled. Cooling is made of the catalyst for butylenes alkylation.

Once the first alkylation reaction of the cycle is completed, the second olefinic reactant, e.g., propylene, is charged to the alkylation reactor in admixture with the butylenes alkylate and excess isobutane therewith accumulated in the first surge tank and the continuously flowing liquid hydrofluoric acid catalyst. The resultant alkylation effluent is continuously separated into a hydrocarbon liquid phase and liquid acid phase as was the alkylate stream of the first alkylation reaction. The HF acid catalyst is temperature-adjusted and continuously recycled to the reactor, as discussed before, and the hydrocarbon phase of the alkylate stream is continuously divided into two streams. The first stream is passed to a second surge tank with the other stream being passed to a fractionator which is continuously operated. The portion of the alkylate stream passed to the fractionator is then fractionated into its various components with alkylate product being recovered and unreacted isoparaffin, i.e., isobutane, being passed to a third surge tank. The second and third surge tanks are storage tanks for holding the particular liquids until needed when the cycle begins all over again. When the cycle begins again with the reaction of the butylenes with isobutane, isobutane in the third surge tank is recycled to the reactor and alkylation hydrocarbon in the second surge tank is passed to the fractionator in order to allow the fractionator to be operated continuously. Total feed or the hydrocarbon (butylenes alkylate and excess isobutane) is passed to the first surge zone. Reactant isobutane for both alkylations is preferably added to the reactor during the first alkylation; however, reactant isobutane can be added to the third surge zone, or to the second alkylation.

The cycle begins again with the alkylation of isobutane (feed isobutane and diluent isobutane) from the first surge zone (butylenes alkylate and isobutane) with propylene. The catalyst is continuously recycled and during propylene alkylation (higher temperature desired than in butylenes alkylation) heating of the catalyst at startup can be effected. After proper temperature is attained in propylene reaction, cooling is effected to remove the heat of reaction to maintain the desired higher temperature. The separated propylene alkylate and isobutane liquid hydrocarbon phase is then again split with one portion going to the fractionator and the other portion going to the second surge tank for holding until the cycle is again repeated with butylenes.

The cyclic process of the invention can also be reversed in that the propylene can be the first olefinic reactant and the butylenes the second olefinic reactant. This would mean that the butylenes would be reacted with the propylene alkylate containing the unreacted isobutane. The entire result can still be optimized by controlling the temperatures in the different HF alkylations as the acid and alkylate are separated and can be heated or cooled accordingly in order to obtain the optimum temperature in the subsequent alkylation. When startup is made with no alkylate and isobutane hydrocarbon available, the feed to the first cycle is the olefin, isobutane, for reacting and diluent, and the catalyst.

The preferred olefins in the process are propylene and butylenes, but any appropriate olefin can be used. Examples of appropriate olefins are the $C_3$ to $C_7$ olefins, depending on the type of alkylate product desired.

Isobutane is the preferred isoparaffin, but any appropriate isoparaffin can be used. Examples of appropriate isoparaffins are the $C_4$ to $C_8$ isoparaffins, depending on the type of alkylate product desired.

Various types of catalyst can be utilized in the process, including sulfuric acid, hydrofluoric acid, phosphoric acid, certain halosulfonic acids, and aluminum chloride. The preferred catalyst, however, is hydrofluoric acid (e.g., 85 to 98 weight percent HF) because of the relative ease with which it can be used and reused and because of the superior quality of the alkylate that is produced.

The invention is not dependent upon specific reaction conditions as these are conventional and well known in the art. However, the mol ratio of isoparaffin to olefin is usually maintained somewhere in the range of 4:1 to 20:1. The volume ratio of acid to hydrocarbon feed can be maintained at about 4:1 but can be varied in the range of 0.5:1 to 6:1. A large volume of acid recycled to the reactors can be utilized as a means of temperature control as well as a catalyst. Alkylation temperature can vary from about 50°–200° F. (10°–93° C.); however, when alkylating isobutane with butylene, a reaction temperature in the range of about 60°–95° F. (15.6°–35° C.) is preferred. When alkylating isobutane with propylene, a temperature in the range of approximately 110°–125° F. (38°–51.5° C.) is preferred.

The particular length of the cycle is not important and any reasonable cycle can be used. The times of each part of the cycle do not have to be equal and will depend upon the quantities of olefins, e.g., butylenes and propylene, available for reaction or that are desired to be used.

The particular type of reactor to be used in the process is not important and many appropriate reactors are known in the art. The preferred reactor, however, is the riser reactor, as in U.S. Pat. No. 3,213,157 of Phillips Petroleum Company.

Referring now to the FIGURE, isobutane feed 10, recycle isobutane 11, and butylenes olefinic reactant feed 12 are charged to the alkylation reactor 31 in the first part of the cyclic process. The hydrocarbon phase and acid phase of the resultant alkylation effluent are continuously separated in settler 32. The separated acid catalyst is continuously recycled to the reactor via conduit means 33 and indirect heat exchanger 50. A portion of the system catalyst can intermittently or continuously be passed via 34 to HF rerun (not shown) and rerun HF returned via 35. The separated hydrocarbon phase is continuously passed by means of 15 and 16 to surge tank 1 designated 17, where it accumulates and is held in storage until needed. The second part of the cyclic process is then initiated by charging propylene olefinic reactant 13 and also the hydrocarbon liquid held in surge tank 1, designated 17, which hydrocarbon comprises alkylate hydrocarbons and unreacted (feed and diluent) isobutane, via 14 to the alkylation reactor in admixture with the alkylation catalyst. The resultant alkylate effluent is continuously separated into a liquid alkylate hydrocarbon phase and a liquid acid phase in settler 32 with the acid phase being continuously recycled via 33. A portion of the hydrocarbon phase is passed via 15 and 19 to fractionator 36 with the remainder of the hydrocarbon phase passed via 15 and 18 to surge tank 2, designated 43. The fractionator separates the charged hydrocarbon into its various components with recovery of alkylate product via 22 and recycle of unreacted isobutane via line 21. The unreacted isobutane is passed via line 21 to surge tank 3, designated 40, where it is held in storage until needed upon repeating the cycle wherein butylenes alkylate isobutane.

When the cycle is repeated, recycle isobutane accumulated in surge tank 3, designated 40, is passed via line 11 along with butylenes feed 12 to the alkylation reactor 31 in admixture with acidic alkylation catalyst. Feed or reactant isobutane feed is added via line 10. During the first part of the cycle, a liquid accumulated in surge tank 2, designated 43, is passed via line 20 to the fractionator 36 wherein the hydrocarbon is fractionated into its various components. This allows the fractionator to be operated continuously with surge tank 2, designated 43, providing alkylate-containing hydrocarbon to be fractionated during this first part of the cycle on butylenes alkylation, and the alkylate-containing hydrocarbon to be fractionated during the second part of the cycle coming directly from the propylene-isobutane alkylation.

The cycle is thereby continually repeated for the desired length of time and with the ability to optimize the reaction conditions in the different HF alkylations even though only one reactor is being used.

Propane, usually present in feed to fractionator 36, is removed continuously at 41 and normal butane vapor is preferably removed at 42.

A calculated example is herewith given using a two-hour total cycle, wherein butylenes effect alkylation of isobutane in the first hour (I) and then propylene effects alkylation of isobutane in the second hour (II). This is a two-hour cycle and only illustrative and is not intended to limit the invention in any way. Any cycle can be used, within reason, and the times of each "partcycle" do not have to be equal.

The example shows butylenes, alkylate, and isobutane being stored in surge tank 1, designated 17, for hour I, and then being the source of the isobutane feed and diluent for propylene alkylation of isobutane during hour II. This cycle could be reversed, and the propylene alkylate containing the isobutane could be stored in surge 1, during hour I (propylene being used to HF alkylate isobutane during hour I in this embodiment); then, in hour II, with butylenes HF alkylating isobutane, this flow from surge tank 1 (propylene alkylate plus isobutane) would be charged to HF alkylation.

Barrels/Hour
Typical Run
(Calculated)

I - One hour on butylenes cycle.
II - One hour on propylene cycle.
I–II - Fractionation is continuous.

-continued

Barrels/Hour
Typical Run
(Calculated)

Total "run" is two-hour cycle.

Hour I:

| Composition | Feed 1 to Reactor | Product to Surge 1 (17) | From Surge 2 to Fractionator | Recycle iC4 to Surge 3 (40) | Alkylate Yield |
|---|---|---|---|---|---|
| Stream Number: | | (16) | (20) | (21) | (22) |
| (13) Propylene | 0 | 0 | 0 | 0 | 0 |
| (12) Butylenes | 100 | 0 | 0 | 0 | 0 |
| (10) Feed isobutane | 200 | 100 | 0 | 0 | 0 |
| (11) Recycle isobutane | 1,000 | 1,000 | 500 | 500 | 0 |
| Alkylate | 0 | 170 | 170 | 0 | 170 |
| Total | 1,300 | 1,270 | 670 | 500 | 170 |

Hour II:

| Composition: | Propylene Feed to Reactor | From Surge 1 (17) to Reactor | Product Yield | Product to Fractionator | Product to Surge 2 (43) | Recycle iC4 to Surge 3 (40) | Alkylate Yield |
|---|---|---|---|---|---|---|---|
| Stream Number: | (13) | (14) | (15) | (19) | (18) | (21) | (22) |
| (13) Propylene | 100 | 0 | 0 | 0 | 0 | — | 0 |
| (12) Butylenes | 0 | 0 | 0 | 0 | 0 | — | 0 |
| (10) Feed Isobutane | 0 | 100 | 0 | 0 | 0 | — | 0 |
| (11) Recycle Isobutane | 0 | 1,000 | 1,000 | 500 | 500 | 500 | 0 |
| Alkylate | 0 | 170 | 340 | 170 | 170 | — | 170 |
| Total | 100 | 1,270 | 1,340 | 670 | 670 | 500 | 170 |

I - iC4/olefin (butylenes) mol ratio = 10.7/1.
II - iC4/olefin (propylene) mol ratio = 8.6/1.
(Propane and normal butane not used in example.)

Two-Hour Cycle on Fractionation (Continuous Flow):

| I + II | Feed Hour I (20) | Feed Hour II (19) | Total in 2 Hours (19 + 20) | Yield Hour I, iC4 (21) | Yield Hour II, iC4 (21) | Yield Hour I, Alkylate (22) | Yield Hour II, Alkylate (22) |
|---|---|---|---|---|---|---|---|
| Composition Bbls/Hr | | | | | | | |
| Stream Number: | | | | | | | |
| (13) Propylene | 0 | 0 | 0 | 0 | 0 | 0 | 0 |
| (12) Butylenes | 0 | 0 | 0 | 0 | 0 | 0 | 0 |
| (10) Feed Isobutane | 0 | 0 | 0 | 0 | 0 | 0 | 0 |
| (11) Recycle Isobutane | 500 | 500 | 1,000 | 500 | 500 | 0 | 0 |
| Alkylate | 170 | 170 | 340 | 0 | 0 | 170 | 170 |
| Total | 670 | 670 | 1,340 | 500 | 500 | 170 | 170 |

Propane and normal butane were left out of material balance to simplify the system's explanation.

Reasonable variations and modifications which will become apparent to those skilled in the art can be made in the present invention without departing from the spirit and scope thereof.

We claim:

1. A process for producing an alkylation reaction product from an isoparaffinic reactant and two different olefinic reactants which comprises:
   passing the isoparaffin reactant and a first olefinic reactant in admixture with an acid alkylation catalyst through an alkylation zone under alkylating conditions to form a first alkylate stream,
   separating said first alkylate stream into a first hydrocarbon phase comprising alkylation products and unreacted isoparaffin and an acid alkylation catalyst phase,
   passing said first hydrocarbon phase to a first surge zone,
   passing a second olefinic reactant and said first hydrocarbon phase in said first surge zone in admixture with an acid alkylation catalyst through said alkylation zone under alkylating conditions to form a second alkylate stream,
   separating said second alkylate stream into a second hydrocarbon phase comprising alkylation products unreacted isoparaffin and an acid alkylation catalyst phase,
   passing a first portion of said second hydrocarbon phase to a fractionation zone and a second portion of said second hydrocarbon phase to a second surge zone,
   passing the accumulated hydrocarbon liquid held in the second surge zone to the fractionation zone after said first portion of second hydrocarbon phase has been fractionated and said alkylation zone has returned to the cycle of passing said first olefinic reactant and isoparaffin through the alkylation zone to form said first alkylate stream,
   recovering alkylate product from said fractionation zone, and
   continuously recycling separated acid alkylation catalyst phase to the alkylation zone with appropriate heating or cooling of said catalyst phase thereby obtaining optimum temperature in the particular alkylation reaction based on said first or said second olefinic reactant.

2. The process of claim 1 comprising the additional steps of:
   passing isoparaffin overhead separated from said fractionation zone to a third surge tank,
   passing the isoparaffin accumulated in said third surge tank as isoparaffinic feed in admixture with said first olefinic reactant and an acid alkylation catalyst to the alkylation zone.

3. A process in accordance with claim 1 wherein said acid alkylation catalyst is hydrofluoric acid.

4. A process in accordance with claim 1 wherein said isoparaffinic reactant is isobutane.

5. A process in accordance with claim 1 wherein said first olefinic reactant comprises butylenes and said second olefinic reactant comprises propylene.

6. A process in accordance with claim 1 wherein said first olefinic reactant comprises propylene and said second olefinic reactant comprises butylenes.

* * * * *